(12) United States Patent
Brestel et al.

(10) Patent No.: US 10,891,731 B2
(45) Date of Patent: Jan. 12, 2021

(54) SYSTEMS AND METHODS FOR PRE-PROCESSING ANATOMICAL IMAGES FOR FEEDING INTO A CLASSIFICATION NEURAL NETWORK

(71) Applicant: Zebra Medical Vision Ltd., Shefayim (IL)

(72) Inventors: Chen Brestel, Rehovot (IL); Eli Goz, Herzlia (IL); Jonathan Laserson, Tel Aviv (IL)

(73) Assignee: Zebra Medical Vision Ltd., Shefayim (IL)

( * ) Notice: Subject to any disclaimer, the term of this patent is extended or adjusted under 35 U.S.C. 154(b) by 136 days.

(21) Appl. No.: 16/269,619

(22) Filed: Feb. 7, 2019

(65) Prior Publication Data

US 2019/0340752 A1 Nov. 7, 2019

Related U.S. Application Data

(63) Continuation-in-part of application No. 15/972,912, filed on May 7, 2018, now Pat. No. 10,706,545.

(51) Int. Cl.
*G06N 3/08* (2006.01)
*G16H 40/20* (2018.01)
(Continued)

(52) U.S. Cl.
CPC .......... *G06T 7/0012* (2013.01); *G06K 9/6267* (2013.01); *G06N 3/08* (2013.01);
(Continued)

(58) Field of Classification Search
None
See application file for complete search history.

(56) References Cited

U.S. PATENT DOCUMENTS

| 5,857,030 A | 1/1999 | Gaborski et al. |
| 10,631,812 B2 * | 4/2020 | Westerhoff .............. G06F 19/00 |

(Continued)

FOREIGN PATENT DOCUMENTS

| WO | WO 2018/015414 | 1/2018 |
| WO | WO 2019/215604 | 11/2019 |

(Continued)

OTHER PUBLICATIONS

Official Action dated Dec. 13, 2019 From the US Patent and Trademark Office Re. U.S. Appl. No. 15/972,912. (37 pages).
(Continued)

*Primary Examiner* — Idowu O Osifade

(57) ABSTRACT

A system for prioritizing patients for treatment, comprising: at least one hardware processor executing a code for: feeding anatomical images into a visual filter neural network for outputting a category indicative of a target body region depicted at a target sensor orientation and a rotation relative to a baseline, rejecting a sub-set of anatomical images classified into another category, rotating to the baseline images classified as rotated, identifying pixels for each image having outlier pixel intensity values denoting an injection of content, adjusting the outlier pixel intensity values to values computed as a function of non-outlier pixel intensity values, feeding each the remaining sub-set of images with adjusted outlier pixel intensity values into a classification neural network for detecting the visual finding type, generating instructions for creating a triage list for which the classification neural network detected the indication, wherein patients are selected for treatment based on the triage list.

20 Claims, 7 Drawing Sheets

(51) Int. Cl.
*G06K 9/62* (2006.01)
*G16H 30/20* (2018.01)
*G06T 7/00* (2017.01)
(52) U.S. Cl.
CPC .............. *G16H 30/20* (2018.01); *G16H 40/20* (2018.01); *G06T 2207/10116* (2013.01)

(56) References Cited

U.S. PATENT DOCUMENTS

| | | | |
|---|---|---|---|
| 2006/0110021 | A1 | 5/2006 | Luo et al. |
| 2010/0284590 | A1* | 11/2010 | Peng .................... G06K 9/3233 382/128 |
| 2011/0188706 | A1* | 8/2011 | Zhou ........................ G06K 9/00 382/103 |
| 2011/0257919 | A1* | 10/2011 | Reiner .................. G06F 19/321 702/81 |
| 2012/0172700 | A1* | 7/2012 | Krishnan ............. A61B 6/5217 600/407 |
| 2013/0129165 | A1 | 5/2013 | Dekel et al. |
| 2015/0049163 | A1* | 2/2015 | Smurro .................... H04N 7/15 348/14.08 |
| 2015/0261915 | A1* | 9/2015 | Yanagida .............. G06F 40/169 382/131 |
| 2015/0262014 | A1* | 9/2015 | Iwamura ................ G16H 30/40 382/128 |
| 2015/0279061 | A1* | 10/2015 | Kutsuna ................ G06T 7/0012 382/131 |
| 2017/0046483 | A1* | 2/2017 | Reicher ................. G06F 16/245 |
| 2017/0221204 | A1 | 8/2017 | Shinagawa |
| 2018/0101645 | A1 | 4/2018 | Sorenson et al. |
| 2018/0259608 | A1 | 9/2018 | Golden et al. |
| 2019/0110753 | A1 | 4/2019 | Zhang et al. |
| 2019/0156484 | A1* | 5/2019 | Nye ........................ G16H 50/20 |
| 2019/0209022 | A1 | 7/2019 | Sobol et al. |
| 2019/0340753 | A1 | 11/2019 | Brestel et al. |
| 2019/0340763 | A1 | 11/2019 | Laserson |
| 2019/0350657 | A1* | 11/2019 | Tolkowsky ............. A61B 90/36 |

FOREIGN PATENT DOCUMENTS

| | | |
|---|---|---|
| WO | WO 2019/215605 | 11/2019 |
| WO | WO 2019/215606 | 11/2019 |

OTHER PUBLICATIONS

International Search Report and the Written Opinion dated Sep. 25, 2019 From the International Searching Authority Re. Application No. PCT/IB2019/053726. (11 Pages).
International Search Report and the Written Opinion dated Sep. 8, 2019 From the International Searching Authority Re. Application No. PCT/IB2019/053725. (9 Pages).
International Search Report and the Written Opinion dated Sep. 12, 2019 From the International Searching Authority Re. Application No. PCT/IB2019/053724. (12 Pages).
Dong et al. "Learning to Read Chest X-Ray Images From 16000+ Examples Using CNN", 2017 Proceedings of the IEEE/ACM International Conference on Connected Health: Applications, Systems and Engineering Technologies, CHASE, Philadelphia, PA, USA, Jul. 17-19, 2017, p. 51-57, Jul. 17, 2017.
Kamnitsas et al. "Efficient Multi-Scale 3D CNN With Fully Connected CRF for Accurate Brain Lesion Segmentation", Medical Image Analysis, 36: 61-78, Available Online Oct. 29, 2016.
Mayer et al. "Transfer Learning for Data Triage Applications", IS&T International Symposium on Electronic Imaging 2018, Visual Information Processing and Communication IX, p. 175-1-175-6, Jan. 1, 2018.
European Search Report and the European Search Opinion dated Sep. 26, 2019 From the European Patent Office Re. Application No. 19173136.3. (8 Pages).
De Vos et al. "ConvNet-Based Localization of Anatomical Structures in 3D Medical Images", ARXIV.Org, Cornell University Library, XP080763925, ArXiv:1704.05629v1, p. 1-12, Apr. 19, 2017.
Brady et al. "Discrepancy and Error in Radiology: Concepts, Causes and Consequences", The Ulster Medical Journal, 81(1): 3-9, Jan. 2012.
Bruno et al. "Understanding and Confronting Our Mistakes: The Epidemiology of Error in Radiology and Strategies for Error Reduction", RadioGraphics, 35(6): 1668-1676, Published Online Oct. 14, 2015.
Demner-Fushman et al. "Annotation of Chest Radiology Reports for Indexing and Retrieval", Proceedings of the First International Workshop on Multimodal Retrieval in the Medical Domain, MRDM '15, Vienna, Austria, Mar. 29, 2015, LNCS 9059: 99-111, Mar. 29, 2015.
Hanna et al. "Effect of Shift, Schedule, and Volume on Interpretive Accuracy: A Retrospective Analysis of 2.9 Million Radiologic Examinations", Radiology, 287(1): 205-212, Published Online Nov. 20, 2017.
Huang et al. "Densely Connected Convolutional Networks", Proceedings of the IEEE Conference on Computer Vision and Pattern Recognition, CVPR '17, Honolulu, Hawaii, USA, Jul. 21-26, 2017, p. 4700-4708, Jul. 21, 2017.
Jing et al. "On the Automatic Generation of Medical Imaging Reports", arXiv:1711.08195v1, p. 1-9, Nov. 22, 2017.
Rajpurkar et al. "CheXNet: Radiologist-Level Pneumonia Detection on Chest X-Rays With Deep Learning", arXiv:1711.05225v1, 7 P., Nov. 14, 2017.
Robinson et al. "Variation Between Experienced Observers in the Interpretation of Accident and Emergency Radiographs", The British Journal of Radiology, 72: (856): 323-330, Apr. 1999.
Shin et al. "Learning to Read Chest X-Rays: Recurrent Neural Cascade Model for Automated Image Annotation", Proceedings of the IEEE Conference of Computer Vision and Pattern Recognition, CVPR '16, Las Vegas, NV, USA, Jun. 27-30, 2016, p. 2497-2506, Jun. 27, 2016.
Taylor et al. "Automated Detection of Moderate and Large Pneumothorax on Frontal Chest X-rays Using Deep Convolutional Neural Networks: A Retrospective Study", PLoS Medicine, 15(11): e1002697, pp. 1-15, Nov. 20, 2018.
Wang et al. "ChestX-Ray8: Hospital-Scale Chest X-Ray Database and Benchmarks on Weakly-Supervised Classification and Localization of Common Thorax Diseases", Proceedings of the IEEE Conference on Computer Vision and Pattern Recognition, CVPR '17, Honolulu, Hawaii, USA, Jul. 21-26, 2017, p. 2097-2106, Jul. 21, 2017.
Official Action dated Sep. 4, 2020 from the US Patent and Trademark Office Re. U.S. Appl. No. 16/269,633. (101 pages).

* cited by examiner

502

504

SYSTEMS AND METHODS FOR PRE-PROCESSING ANATOMICAL IMAGES FOR FEEDING INTO A CLASSIFICATION NEURAL NETWORK

RELATED APPLICATIONS

This application is a Continuation-In-Part (CIP) of U.S. patent application Ser. No. 15/972,912 filed on May 7, 2018.

This application is also related to and co-filed U.S. Continuation-In-Part (CIP) Patent Application, titled "SYSTEMS AND METHODS FOR DETECTING AN INDICATION OF A VISUAL FINDING TYPE IN AN ANATOMICAL IMAGE".

The contents of the above applications are all incorporated by reference as if fully set forth herein in their entirety.

FIELD AND BACKGROUND OF THE INVENTION

The present invention, in some embodiments thereof, relates to medical anatomical images and, more specifically, but not exclusively, to systems and methods for pre-processing images for feeding into a classification neural network.

Manual visual assessment (e.g., by a radiologist) of medical anatomical images, such as x-ray images, is a challenging and time consuming task due to the large amount of information that needs to be processed. The radiologist looks to identify relevant features of the anatomical images when a large number of possible features are possible. For example, each medical anatomical image includes multiple anatomical objects, such as bones, different organs, and different connective tissues, each of which may present with different findings. Critical findings, which require urgent treatment, may be missed by the radiologist.

SUMMARY OF THE INVENTION

According to a first aspect, a system for prioritizing patients for treatment for an acute medical condition requiring early and rapid treatment thereof based on a created a triage list of anatomical images likely depicting a visual finding type indicative of the acute medical condition, comprises: at least one hardware processor executing a code for: feeding each one of a plurality of anatomical images into a visual filter neural network for outputting a classification category indicative of a target body region depicted at a target sensor orientation and a rotation relative to a baseline, rejecting a sub-set of the plurality of anatomical images classified into another classification category, rotating to the baseline a remaining sub-set of the plurality of anatomical images classified as rotated relative to the baseline, identifying pixels for each respective image of the plurality of anatomical images having outlier pixel intensity values denoting an injection of content, adjusting the outlier pixel intensity values of the identified pixels to values computed as a function of non-outlier pixel intensity values, feeding each one of the remaining sub-set of the plurality of anatomical images with adjusted outlier pixel intensity values into a classification neural network for detecting the visual finding type, generating instructions for creating a triage list for which the classification neural network detected the indication, wherein patients likely suffering from the acute medical condition denoted by the indication are selected for early and rapid treatment thereof based on the triage list.

According to a second aspect, a system for training a visual filter neural network for selection of anatomical images for inputting into a classification neural network for detecting a visual finding type indicative of an acute medical condition for early and rapid treatment thereof, comprises: receiving a target body region and a target sensor orientation of a target anatomical image defined by the classification neural network, creating a training dataset by labeling each one of a plurality of anatomical images stored by a medical imaging storage server with a respective label indicative of a target body region captured at a target sensor orientation defined by the classification neural network and a rotation relative to a baseline, or with a respective label indicative of at least one of a non-target body region and a non-target sensor orientation, and training the visual filter neural network based on the training dataset, for classifying a target anatomical image into a classification category indicative of the target body region depicted at the target sensor angle and the rotation relative to the baseline, or into another classification category indicative of at least one of a non-target body region and a non-target sensor orientation, wherein the target anatomical image is rejected when classified into the another classification category, and the target anatomical image is rotated to the baseline and inputted into the classification neural network for detecting the visual finding type when classified into the target body region depicted at the target sensor angle and the rotation relative to the baseline.

According to a third aspect, a system for increasing accuracy of a classification neural network in detecting a visual finding type indicative of an acute medical condition for early and rapid treatment thereof, comprising at least one hardware processor executing a code for: receiving a plurality of anatomical images from a medical imaging storage server, feeding each one of the plurality of anatomical images into a visual filter neural network for outputting a classification category indicative of a target body region depicted at a target sensor orientation and a rotation relative to a baseline defined by the classification neural network, or another classification category indicative of at least one of a non-target body region and a non-target sensor orientation, rejecting a sub-set of the plurality of anatomical images classified into the another classification category, to obtain a remaining sub-set of the plurality of anatomical images, rotating to the baseline the remaining sub-set of the plurality of anatomical images classified as rotated relative to the baseline, creating a training dataset from the remaining sub-set of the plurality of anatomical images, and training a classification neural network according to the training dataset for detecting the visual finding type indicative of the acute medical condition for early and rapid treatment thereof.

According to a fourth aspect, a system for increasing accuracy of a classification neural network in detecting a visual finding type indicative of an acute medical condition for early and rapid treatment thereof, comprises: at least one hardware processor executing a code for: receiving a plurality of anatomical images from a medical imaging storage server, feeding each one of the plurality of anatomical images into a visual filter neural network for outputting a classification category indicative of a target body region depicted at a target sensor orientation and a rotation relative to a baseline defined by the classification neural network, or another classification category indicative of at least one of a non-target body region and a non-target sensor orientation, rejecting a sub-set of the plurality of anatomical images classified into the another classification category, to obtain a remaining sub-set of the plurality of anatomical images, rotating to the baseline the remaining sub-set of the plurality of anatomical images classified as rotated relative to the baseline, and feeding each one of the remaining sub-set of the plurality of anatomical images into the classification neural network for detecting the visual finding type indicative of the acute medical condition for early and rapid treatment thereof.

In a further implementation form of the first, second, third, and fourth aspects, accuracy of the classification neural network in detecting the visual finding type indicative of the acute medical condition is increased for the remaining sub-set of the plurality of anatomical images in comparison to detecting the visual finding type for the plurality of anatomical images by the classification neural network without rejection of any anatomical images by the visual filter neural network.

In a further implementation form of the first, second, third, and fourth aspects, accuracy of the classification neural network in detecting the visual finding type indicative of the acute medical condition is increased for the remaining sub-set of the plurality of anatomical images with adjusted outlier pixel intensity values and rotation to baseline, in comparison to detecting the visual finding type for the plurality of anatomical images by the classification neural network without rejection of any anatomical images by the visual filter neural network, without adjustment of outlier pixel intensity values, and without rotation to baseline.

In a further implementation form of the first, second, third, and fourth aspects, the system further comprises code for and/or the method further comprises at least one of: diagnosing the acute medical condition and treating the patient for the acute medical condition.

In a further implementation form of the first, second, third, and fourth aspects, the visual filter neural network selects chest x-rays depicting at least one of AP and PA orientation, and rejects at least one of non-chest x-rays and lateral orientation.

In a further implementation form of the first, second, third, and fourth aspects, the visual filter neural network is installed client-side, on a client terminal in communication with the medical imaging storage server over a network, wherein the client terminal hosts the classification neural network.

In a further implementation form of the first, second, third, and fourth aspects, a single classification category is indicative of the depicted body region, the target sensor orientation and the rotation relative to the baseline.

In a further implementation form of the first, second, third, and fourth aspects, the classification neural network is trained according to a training dataset of training anatomical medical images that were not rejected by the visual filter neural network, had outlier pixel intensity values denoting injected content adjusted, and rotated to the baseline.

In a further implementation form of the first, second, third, and fourth aspects, the visual filter neural network outputs the classification category further indicative of a target imaging modality type or the another classification category further indicative of a non-target imaging modality type, wherein the rejected sub-set of the plurality of anatomical images include anatomical images classified into the another classification category.

In a further implementation form of the first, second, third, and fourth aspects, the plurality of anatomical images are stored by a medical imaging server according to a medical imaging storage format, and wherein the visual filter neural network rejects the sub-set of the plurality of anatomical images independently of metadata defined by the medical imaging storage format and associated with the respective anatomical image.

In a further implementation form of the first, second, third, and fourth aspects, the medical imaging server comprise a PACS server, the medical imaging storage format is DICOM®, and the metadata of DICOM® stores an indication of the target body region and the target sensor orientation.

In a further implementation form of the first, second, third, and fourth aspects, the adjusting is performed for the respective image having outlier pixel intensity values stored with a pixel depth, that is different than a pixel depth of the respective image when presented on a display.

In a further implementation form of the first, second, third, and fourth aspects, the system further comprises code for and/or the method further comprises computing, for each respective image, a histogram of pixel intensity values, wherein the outlier pixel intensity values are selected based on one or two extreme bins of the histogram that are spaced apart from another bin by an empty bin that does not include any pixels.

In a further implementation form of the first, second, third, and fourth aspects, the outlier pixel intensity values are adjusted to a value computed as a function of the another bin and all pixels in the respective image.

In a further implementation form of the first, second, third, and fourth aspects, the function is computed one of: (i) a minimum of the pixel intensity values in the another bin, less a constant multiplied by the median pixel intensity values of all pixels in the respective image, and (ii) a maximum of the pixel intensity values in the another bin, added to a constant multiplied by the median pixel intensity values of all pixels in the respective image, and (iii) a smallest interest such that two raised to the smallest integer minus one is greater than the maximum of the pixel intensity values in the another bin.

In a further implementation form of the first, second, third, and fourth aspects, the classification neural network comprises a single-label neural network computed by at least one of fine-tuning and retraining a trained multi-label neural network according to a single-label training dataset of a plurality of anatomical images labeled with an indication of the visual finding type, wherein the multi-label neural network is trained to compute likelihood of each of a plurality of visual finding types based on a multi-label training dataset storing a plurality of anatomical images labeled with the plurality of visual finding types.

In a further implementation form of the first, second, third, and fourth aspects, the system further comprises code for and/or the method further comprises providing a plurality of classification neural networks, each designed for processing anatomical images of a certain combination of a plurality of combinations of target body region and target sensor orientation, providing a plurality of visual filter neural networks, each designed for classification of anatomical images into a classification category indicative of the certain combination of the plurality of combinations, wherein each certain visual filter neural network corresponds to a certain classification neural network, and feeding the plurality of anatomical images into each one of the plurality of classification neural networks to obtain a respective sub-set of the plurality of anatomical images, and feeding each respective sub-set of the plurality of anatomical images into the corresponding classification neural network.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
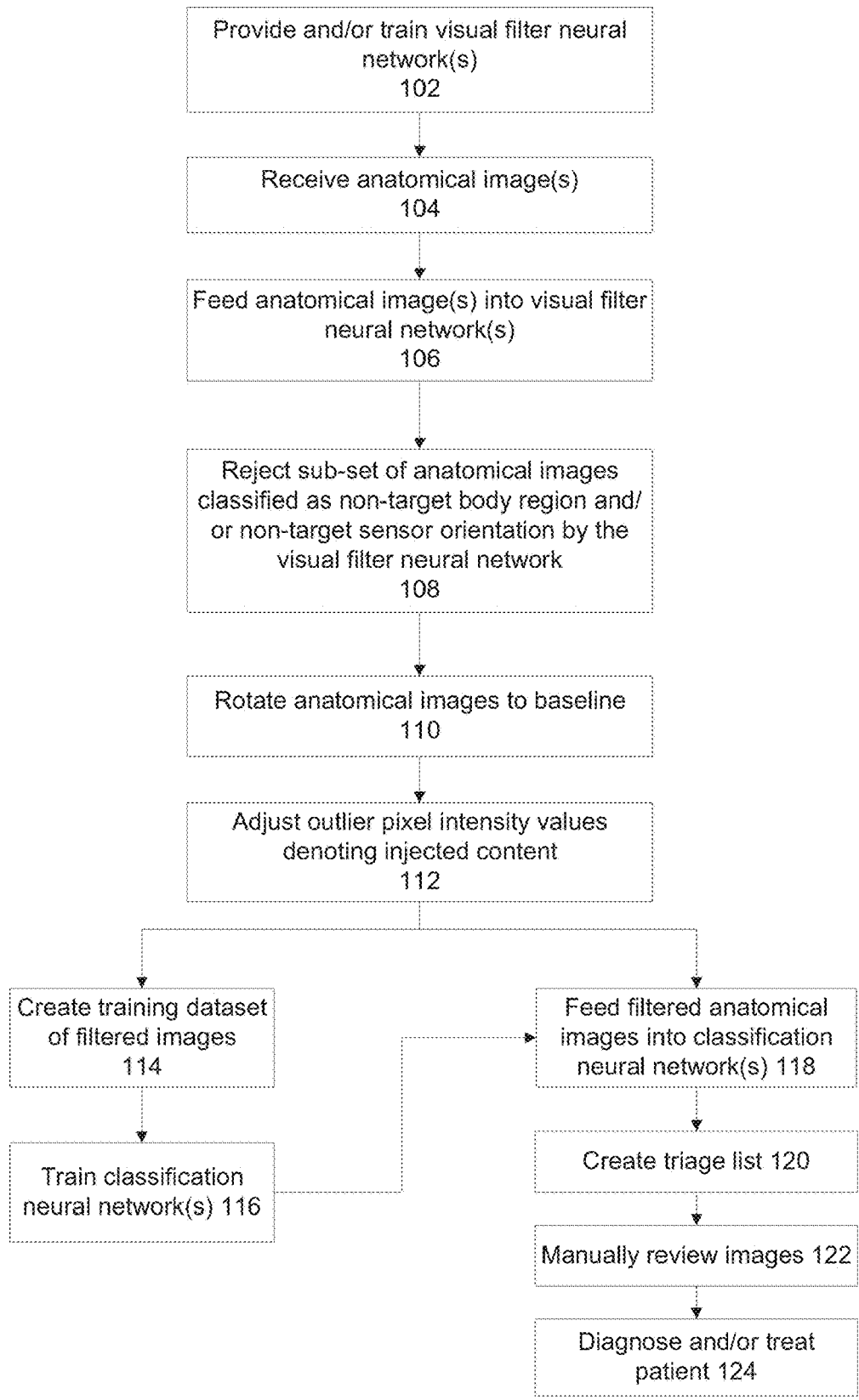
FIG. 1 is a flowchart of a process for adjusting pixel intensity values of injected content of anatomical images and/or using a visual filter neural network to exclude irrelevant anatomical images from being fed into a classification neural network that outputs an indication of likelihood of a visual finding type being depicted in the received anatomical image, in accordance with some embodiments of the present invention.

The present invention, in some embodiments thereof, relates to medical anatomical images and, more specifically, but not exclusively, to systems and methods for pre-processing images for feeding into a classification neural network.

As used herein, the term sensor orientation refers to the orientation of the patient relative to the imaging modality sensor and/or receiver (e.g., Anterior-posterior (AP), PA, lateral), and may include the anatomical orientation of the body of the patient during capture of the image (e.g., left lateral decubitus, supine).

An aspect of some embodiments of the present invention relates to systems, methods, an apparatus, and/or code instructions (i.e., stored on a data storage device and executable by one or more hardware processor(s)) for treatment of a patient suffering from an acute medical condition requiring early and rapid treatment thereof (e.g., pneumothorax, fracture, acute appendicitis, pneumoperitoneum, pneumomediastinum) based on a created a triage list of anatomical images likely depicting a visual finding type indicative of the acute medical condition. Anatomical images are obtained, optionally from a medical imaging server, such as a PACS server storing images according to the DICOM® format. Each one of the anatomical images is fed into a visual filter neural network for outputting a classification category indicative of a target body region depicted at a target sensor orientation and a rotation relative to a baseline, for example, AP/PA chest x-ray, rotated by 90 degrees clockwise. The target body region depicted at target sensor orientation is defined by the classification neural network architecture, for example, designed to detect pneumothorax in AP/PA chest x-rays. A sub-set of the anatomical images classified into another classification category (i.e., not the classification category indicative of the target body region and sensor orientation) is rejected. Anatomical images classified as rotated from baseline are rotated back to baseline. Pixels of images having outlier pixel intensity values denoting an injection of content are identified. Injected content may include, for example, text and/or metadata injected into the image, such as patient ID, image data (e.g., imaging modality, type of image), and letters indicating side of the patient. The outlier pixel intensity values of the identified pixels are adjusted to values computed as a function of non-outlier pixel intensity values. It is noted that the pixel adjustment may be performed before and/or after processing by the visual filter neural network, and before and/or after rotation. The remaining sub-set of the anatomical images (which have passed through the visual filter neural network i.e., non-rejected, have been rotated, and with adjusted outlier pixel intensity values) are into the classification neural network for detecting the visual finding type. Instructions are generated for creating a triage list for which the classification neural network detected the indication, optionally ranked based on likelihood (e.g., probability) of the indication being depicted in the respective image. Patients likely suffering from the acute medical condition denoted by the indication are selected for early and rapid treatment thereof based on the triage list, for example, based on a radiologist (or other healthcare worker) reviewing the images according to the triage list and/or based on a physician examining the patients according to the triage list.

An aspect of some embodiments of the present invention relates to systems, methods, an apparatus, and/or code instructions (i.e., stored on a data storage device and executable by one or more hardware processor(s)) for increasing accuracy of a classification neural network in detecting a visual finding by a visual filter neural network used to filter irrelevant anatomical images prior to feeding into the classification neural network and/or the visual filter neural network used to exclude irrelevant anatomical images from a training dataset for training the classification neural network. Multiple anatomical images are obtained, for example, from a storage server such as a PACS server. Each of the anatomical images is fed into a visual filter neural network. The visual filter neural network may output a classification category indicating that the anatomical image is relevant for being fed into the classification neural network. The classification category denotes that the respective anatomical image depicts a target body region (e.g., chest) and/or a target sensor orientation (e.g., AP/PA), and/or a rotation relative to a baseline rotation (e.g., 90 degree clockwise, 180 degrees, 270 degree clockwise). Alternatively or additionally, the visual filter neural network may output another classification category indicative that the respective anatomical image depicts a non-target body region (e.g., non-chest) and/or a non-target sensor orientation (e.g., non-AP/PA). The images classified into the other classification category are rejected, leaving a remaining sub-set of anatomical images. Images of the remaining-subset classified as being rotated are re-rotated back to baseline. The remaining sub-set of anatomical images (which include the images rotated back to baseline) are fed into the classification neural network, and/or are used to create a training dataset for training the classification neural network.

Optionally, images for including in the training dataset for training the classification neural network are rotated to baseline and/or processed to adjust outlier pixel intensity values denoting injected content.

Optionally, the classification neural network may detect an indication of likelihood of a visual finding being depicted in the received anatomical image. The visual finding may denotes an acute medical condition for early and rapid treatment thereof, for example, pneumothorax, pneumoperitoneum, pneumomediastinum, and fracture.

An aspect of some embodiments of the present invention relates to systems, methods, an apparatus, and/or code instructions (i.e., stored on a data storage device and executable by one or more hardware processor(s)) for training a visual filter neural network for selection of anatomical images for inputting into a classification neural network and/or for selection of anatomical images for creating a training dataset for training the classification neural network. A target body region and/or a target sensor orientation are defined according to the classification neural network. The classification neural network has been trained to process anatomical images having the target body region and/or target sensor orientation for detecting likelihood of the visual finding. A training dataset is created from anatomical images (e.g., stored in a storage server, such as a PACS server) labeled with an indication of the target body region and target sensor orientation and rotation relative to baseline, or with a label indicative of non-target body region and/or non-target sensor orientation. The visual filter neural network is trained based on the training dataset, for classifying a target anatomical image into a classification category indicative of the target body region depicted at the target sensor angle and a rotation relative to the baseline, or into another classification category indicative of a non-target body region and/or a non-target sensor orientation.

Optionally, the visual filter neural network is installed client-side, on the client terminal in communication with the medical imaging storage server (e.g., PACS server). The client terminal hosts the classification neural network. The client terminal (or another client terminal) presents the results of the analysis by the classification neural network that is fed the filtered anatomical images.

Optionally, pixels of the anatomical images (before and/or after being passed through the visual filter neural network, before and/or after rotation) having outlier pixel intensity values are identified. The outlier pixel intensity values are indicative of injected content, for example, patient name, patient ID, and left or right side. The pixel intensity values of the identified outlier pixels are adjusted to values computed as a function of non-outlier pixel intensity values. By adjusting the pixel intensity values of the most extreme values, the dynamic range is improved, improve the ability of the classification neural network to detect fine features.

As described here in additional detail, for example, in the "Examples" section below, Inventors discovered that using visual filter neural network to exclude irrelevant images (i.e., images that do not conform to the target body region and/or target sensor orientation and/or target anatomical imaging modality set for the classification neural network) increases the accuracy of the classification neural network in detecting likelihood of the respective anatomical image depicting a visual finding type. The accuracy is increased when the visual filter neural network is used to exclude images from a training dataset used to train the classification neural network, and/or exclude images from being fed into the classification neural network. The accuracy is increased in comparison to using the classification neural network without passing the anatomical images through the visual filter neural network and/or in comparison to training the classification neural network on a training dataset created from the images without passing the anatomical images through the visual filter neural network.

Inventors discovered that adjusting the values of identified outlier pixel intensity values denoting injected content results in an increased accuracy of the classification neural network in detecting likelihood of a visual finding type being depicted in the respective anatomical image, and/or results in the increased accuracy of detecting the visual finding type when the classification neural network is trained using a training dataset of images for which identified outlier pixel intensity values have been adjusted. The adjustment of the extreme pixel intensity values improves the dynamic range, and/or improves accuracy of the classification neural network in detecting fine features that would otherwise be difficult to detect when the original pixel intensity values are maintained.

The pixel intensities of an x-ray image usually lie in a smooth and continuous range (also termed herein as the normal range). In contrast, artificial pixels that were injected synthetically (e.g., text labels, such as patient ID, patient name, indication of patient side (left or right)), have gray levels that lie far above or below the above mentioned range, and as a result could skew the computation of the network. These outlier pixel intensities are adjusted as described herein, to an intensity level that is closer to the normal range.

It is noted that the highest accuracy may be achieved with a combination of using the visual filter NN and/or rotating the images to baseline and/or adjusting the outlier pixel intensity values denoting injected for creating the training dataset for training the classification neural network, and/or for processing images being fed into the trained classification neural network.

At least some of the systems, methods, apparatus, and/or code instructions described herein address the medical problem of increasing accuracy of a classification neural network in detecting a visual finding in a medical image indicative of a medical problem. The visual finding may be an acute finding, which is not normally present, and representing a medical problem. The acute finding may progress or remain stable, but in either case it may be indicative of a situation that in which the clinical state of the patient is worsening. The acute finding may be indicative of the need for urgent medical treatment. Delay in treatment of the acute finding leads to increases in complications for the patient. The visual finding may be a fine feature, which may be easily missed by a radiologist. Examples of such acute, fine, easily missed visual findings include: pneumothorax in a chest x-ray, pneumomediastinum in a chest x-ray, and pneumoperitoneum in an abdominal x-ray, and fracture in a limb x-ray.

The improvement provided by at least some of the systems, methods, apparatus, and/or code instructions described herein may include a reduction in the amount of time for alerting a user (e.g., treating physician) to the presence of a visual finding type in an anatomical image for rapid diagnosis and/or treatment thereof.

At least some of the systems, methods, apparatus, and/or code instructions described herein improve the technical field of automated analysis of anatomical images by neural networks to identify likelihood of the presence of a visual finding in a medial image, optionally a fine visual finding, optionally representing an acute medical condition requiring urgent diagnosis and treatment, which may easily be missed by a radiologist. The improvement is to the field of neural networks and/or image processing. To identify such visual findings in anatomical images requires a classifier with high accuracy, which is not provided by any standard classifier. Such standard classifiers use an off the shelf classifier (e.g., neural network), and a training dataset of labeled anatomical images. The visual filter neural network, which excludes irrelevant images increases the accuracy of the classification neural network, directly by excluding the irrelevant images from being fed into the classification neural network, and/or indirectly by excluding the irrelevant images from the training dataset used to train the classification neural network which increases the accuracy of the trained classification neural network.

The process of adjusting pixel intensity values of outlier pixels denoting injected content increases the accuracy of the classification neural network, directly by adapting the pixel intensity values of images being fed into the classification neural network, and/or indirectly by adapting the pixel intensity values of images of the training dataset used to train the classification neural network which increases the accuracy of the trained classification neural network. The increase in accuracy may be at least due to the formation of a 'pure' image by removal of 'noise' in the form of the injected content. The injected content, for example, objects placed next to the patient for calibration, patient name and/or patient ID, and letter indicating left and/or right side, represent content irrelevant to detection of a visual finding type in the anatomical images. Presence of the injected content results in extra 'noise' for the classifier neural network to process, which reduces accuracy without benefit. Removal of the noisy injected content increases the accuracy of the classifier neural network. It is noted that the injected content may be removed for creating the training dataset. In which case, the classification neural network trained on the training dataset with removed injected content, has an increase in accuracy when processing target anatomical images that have been processed to remove injected content.

The accuracy of the classification neural network in detecting likelihood of a visual finding type being depicted in a target anatomical image is further improved by the visual filter neural network which removes dependence on DICOM® metadata (and/or other corresponding metadata of other medical data storage formats) that would otherwise be required. Classification neural networks operating without the visual filter neural network are based on access to the DICOM® metadata in order to determine the body portion depicted in the target anatomical image, and/or the sensor orientation at which the target anatomical image is captured and/or the imaging modality type used to capture the image. DICOM® metadata may be erroneous and/or missing, lowering the accuracy of providing the relevant image for processing by the relevant classification neural network, which leads to an overall lower accuracy of the classification neural network in correctly classifying the target anatomical image. In contrast, the visual filter neural network described herein does not use DICOM® metadata (and/or other corresponding metadata of other storage formats). The visual filter neural network excludes irrelevant images and/or includes relevant images from the actual (e.g., raw) image alone without relying on DICOM® metadata. The disconnect from the DICOM® metadata indirectly increases the accuracy of the classification neural network by removing erroneous and/or missing DICOM® metadata as a source of error.

The visual filter neural network may be installed client-side, optionally on the client terminal executing the classification neural network corresponding to the visual filter neural network. The client-side installation is in contrast to server-side installations of standard applications that work with the imaging server (e.g., PACS). For example, applications that integrated with the PACS server and/or PACS viewer. The visual filter neural network is independent of the PACS viewer used by a client terminal to view images stored on the PACS server. The client-side installation architecture described herein enables generation of multiple different types of visual filter neural networks, each for a corresponding classification neural network, all of which are fed from the same set of anatomical images stored on the storage server. For example, the same x-rays are fed to one filter neural network for excluding non-chest and non-AP/PA x-ray (e.g., lateral view) which is associated with a classification neural network to detect pneumothorax, and to another filter neural network for excluding non-supine view abdominal x-rays for detecting pneumoperitoneum. Moreover, the client-side architecture disconnects the visual filter neural network from reliance on the imaging server and/or image viewer, for example, not relying on DICOM® metadata.

At least some of the systems, methods, apparatus, and/or code instructions described herein improve the medical process of diagnosis and/or treatment of acute medical conditions in a patient, for example, within an emergency room setting. At least some of the systems, methods, apparatus, and/or code instructions described herein provide a triage system that identifies likelihood of anatomical images (e.g., chest x-rays) including a visual finding indicating an acute medical condition requiring urgent treatment, for example, pneumothorax. The medical images having identified visual findings are triaged for priority viewing by a healthcare professional (e.g., radiologist, emergency room physician), for example, by ranking according to a priority score, for example, probability of the respective image having the visual finding. For example, images likely having pneumothorax visual findings are prioritized, optionally according to computed probability of having the pneumothorax visual finding. The triage system enables rapid diagnosis of pneumothorax, which leads to rapid treatment of the pneumothorax, saving the patient from complication of delayed treatment of pneumothorax and/or missing the pneumothorax entirely. The triage system is enabled, at least due to the visual filter neural network that excludes irrelevant images from being fed into the classification neural network, and/or by the visual filter neural network that excludes irrelevant images from being included in the training dataset for training the classification neural network, and/or by the process of adapting outlier pixel intensity values of injected content of anatomical images being fed into the classification neural network and/or included in the training dataset.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 2:
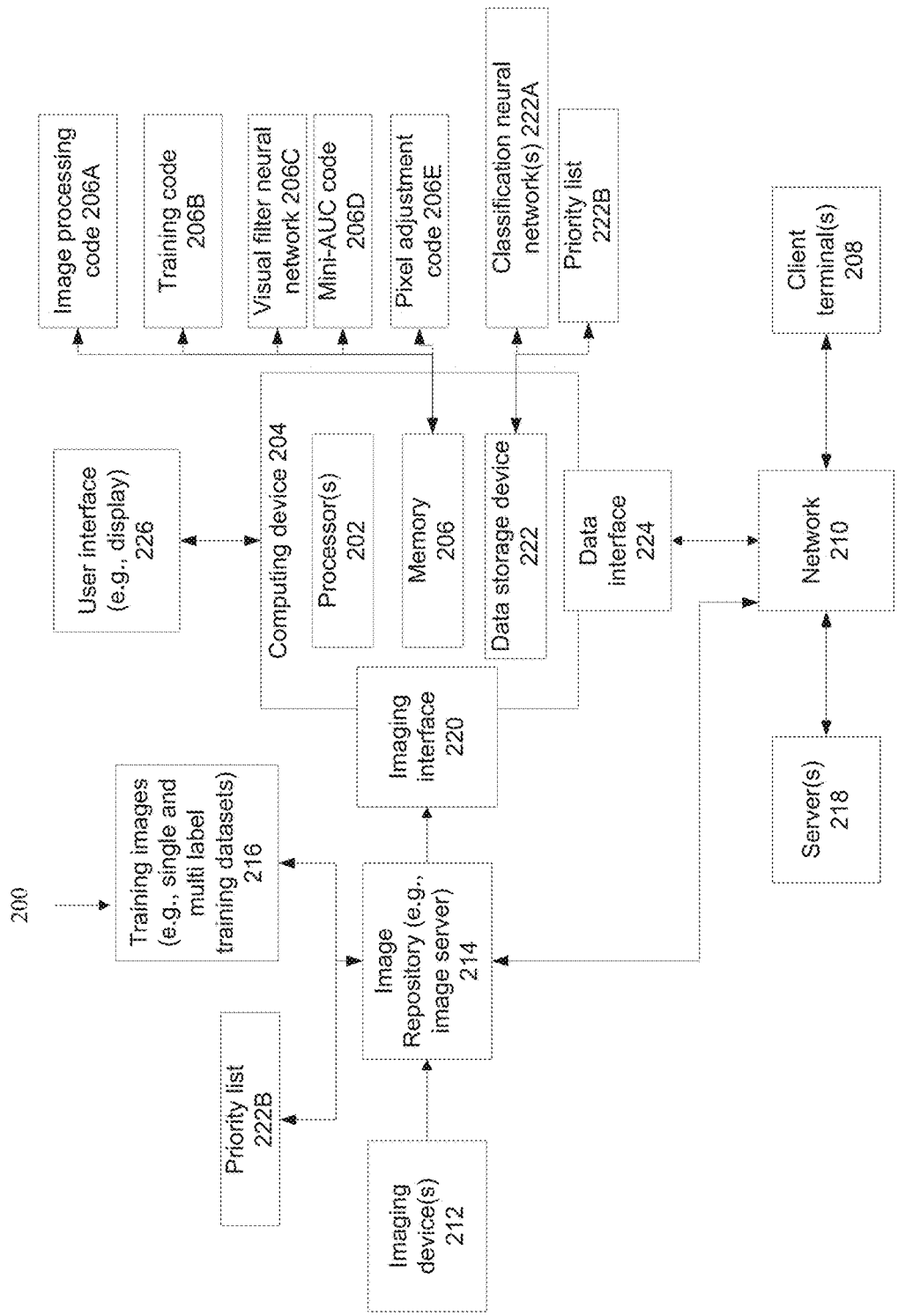
FIG. 2 is a diagram of components of a system for adjusting pixel intensity values of injected content of anatomical images and/or using a visual filter neural network to exclude irrelevant anatomical images from being fed into a classification neural network and/or for training the visual filter neural network and/or for creating the visual filter neural network, in accordance with some embodiments of the present invention.
Figure 3:
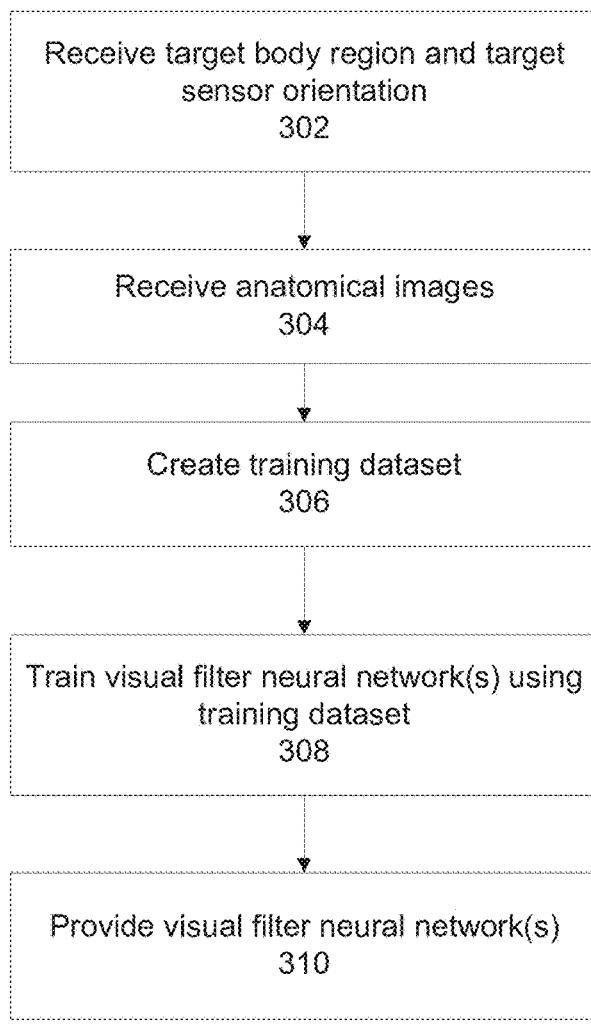
FIG. 3 is a flowchart of a process for creating the visual filter neural network, in accordance with some embodiments of the present invention.

Reference is now made to FIG. 1, which is a flowchart of a process for adjusting pixel intensity values of injected content of anatomical images and/or using a visual filter neural network to exclude irrelevant anatomical images from being fed into a classification neural network that outputs an indication of likelihood of a visual finding type being depicted in the received anatomical image, in accordance with some embodiments of the present invention. FIG. 1 also depicts a process for using the visual filter neural network to exclude irrelevant anatomical images from being included in the training dataset used to train the classification neural network. The visual filter neural network increases accuracy of the classification neural network. Reference is also made to FIG. 2, which is a diagram of components of a system 200 for adjusting pixel intensity values of injected content of anatomical images and/or using a visual filter neural network to exclude irrelevant anatomical images from being fed into a classification neural network and/or for training the visual filter neural network and/or for creating the visual filter neural network, in accordance with some embodiments of the present invention. System 200 also includes components for using the visual filter neural network to exclude irrelevant anatomical images from being included in the training dataset used to train the classification neural network. Reference is also made to FIG. 3, which is a flowchart of a process for creating the visual filter neural network, in accordance with some embodiments of the present invention.

System 200 may implement the acts of the method described with reference to FIG. 1 and/or FIG. 3, optionally by a hardware processor(s) 202 of a computing device 204 executing code instructions stored in a memory 206.

An exemplary implementation of an x-ray triage system is now described to help understand system 200. In a busy emergency room, many chest x-rays of different patients are captured by imaging device 212 and stored in a PACS server 214. Computing device computes a likelihood of each chest x-ray depicting a single visual finding type denoting pneumothorax by trained a classification neural network 222A. Optionally, classification neural network 222A is a single-label neural network computed from a multi-label neural network using a respective multi-label training dataset and a single-label training dataset, as described with reference to co-filed Application. The performance of the classification neural network in terms of target sensitivity and/or target specificity may be obtained by mini-AUC code, as described herein. Prior to computation by classification neural network 222A, each anatomical image (e.g., chest x-ray) is be processed by visual filter neural network 206A for exclusion of irrelevant images (e.g., non-chest x-rays, and/or non-x-ray images and/or non AP-PA images). The chest x-ray images (before or after filtering) may be further processed for removal of outlier pixel intensity values and/or adjusting pixel intensity values by executing pixel adjustment code 206E. The system provides a triage of the anatomical images, by generating a priority worklist 222B. The worklist 222B is generated by ranking the chest x-rays according to a priority score computed based on the likelihood. The higher the probability that a certain chest x-ray has a visual finding indicating pneumothorax, the higher the ranking on the worklist. A healthcare practitioner (e.g., radiologist, ER physician) checks the worklist 222B, and reviews the anatomical images on a display of client terminal 208, for the presence of pneumothorax, starting from the top. The healthcare practitioner is directed to the most urgent chest x-rays most likely to have a visual finding indicative of pneumothorax, reducing the time to diagnose and treat the patient for the pneumothorax in comparison to standard systems that do not provide the triage feature. Patients determined to have pneumothorax may be treated by a physician to remove the excess air.

Computing device 204 may be implemented as, for example, a client terminal, a server, a virtual server, a radiology workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or other devices for presenting indications of the visual finding type to the radiologist.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., client terminal used by a user for viewing anatomical images, remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application, and/or providing functions using a remote access session to the client terminals 208, such as through a web browser.

Client terminal(s) 208 may be implemented as, for example, a radiology workstation, a desktop computer (e.g., running a PACS viewer application), a mobile device (e.g., laptop, smartphone, glasses, wearable device), and nurse station server. Is it noted that the training of the visual filter neural network, and the application of the visual filter neural network to exclude irrelevant anatomical images, may be implemented by the same computing device 204, and/or by different computing devices 204, for example, one computing device 204 trains the visual filter neural network and, and transmits the trained visual filter neural network to a server device 204.

Computing device 204 receives 2D images, and/or 2D slices (optionally extracted from 3D imaging data) captured by an anatomical imaging device(s) 212, for example, an x-ray machine, a magnetic resonance imaging (MRI) device, a computer tomography (CT) machine, and/or an ultrasound machine. Anatomical images captured by imaging machine 212 may be stored in an image repository 214, for example, a storage server (e.g., PACS server), a computing cloud, virtual memory, and a hard disk. The anatomical images stored by image repository 214 may include images of patients optionally associated with text based radiology reports. Training images 216 are created based on the captured anatomical images and text based radiology reports, as described herein.

Training images 216 may be used to train the visual filter neural network, as described herein. As used herein, the term training images and training dataset may be interchanged. It is noted that training images 216 may be stored by a server 218, accessibly by computing device 204 over network 210, for example, a publicly available training dataset, and/or a customized training dataset created for training the visual filter neural network, as described herein.

Anatomical images captured by imaging machine(s) 212 depict internal anatomical features and/or anatomical structures within the body of the target patient.

Exemplary anatomical images include 2D x-ray images captured by an x-ray machine. Exemplary x-ray anatomical images include: AP and PA views of the chest, abdominal x-rays, and x-rays of limbs. Selected views of the x-ray images may be defined as the best view for detecting the visual finding type.

Computing device 204 may receive the anatomical images for filtering, and/or receive training images 216, from imaging device 212 and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store image processing code 206A that implement one or more acts and/or features of the method described with reference to FIG. 1, and/or training code 206B that execute one or more acts of the method described with reference to FIG. 3, and/or code instructions of trained classification neural network 222A and/or code of visual filter neural network code 206C for filtering the anatomical images prior to processing by the trained single-label neural network and/or prior to being used for training the single-label and/or multi-label neural network and/or mini-AUC code 206D for selecting single-label neural networks according to a target sensitivity and/or specificity and/or pixel adjustment code 206E for adjusting pixel intensity values for removal of outliers, as described herein.

Alternatively or additionally, client terminal(s) may locally store and/or execute image processing code 206A, visual filter neural network 206C, and/or code instructions of trained classification neural network 222A and/or priority list 222B and/or mini-AUC code 206D and/or pixel adjustment code 206E.

Computing device 204 may include a data storage device 222 for storing data, for example, code instructions of trained classification neural network 222A, priority list 222B (generated as described herein), visual filter neural network 206C, mini-AUC code 206D, and/or training images 216. Data storage device 222 may be implemented as, for example, a memory, a local hard-drive, a removable storage device, an optical disk, a storage device, and/or as a remote server and/or computing cloud (e.g., accessed over network 210). It is noted code instructions of trained classification neural network 222A, visual filter neural network 206C, training images 216, priority list 222B, and/or mini-AUC code 206D, and/or pixel adjustment code 206E may be stored in data storage device 222, with executing portions loaded into memory 206 for execution by processor(s) 202.

Optionally, priority list 222B is provided to image server 214, for example, for instructing the priority presentation of images stored by image server 214. Alternatively or additionally, computing device 204 provides instructions for image server 214 to generate priority list 222B.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training images 216 and/or to download an updated version of image processing code, training code, visual filter neural network, and/or the trained classification neural network.

It is noted that imaging interface 220 and data interface 224 may be implemented as a single interface (e.g., network interface, single software interface), and/or as two independent interfaces such as software interfaces (e.g., as application programming interfaces (API), network ports) and/or hardware interfaces (e.g., two network interfaces), and/or combination (e.g., single network interface, and two software interfaces, two virtual interfaces on a common physical interface, virtual networks on a common network port). The term/component imaging interface 220 may sometimes be interchanged with the term data interface 224.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server that computes likelihood of the visual finding in anatomical images, provides the image storage server with the computed likelihood for determining a priority score of the respective anatomical image for creating the priority list, and where the highest ranked anatomical images are viewed on a display of the client terminal 208.

Server 218. In one implementation, server 218 is implemented as image server 214, for example, a PACS server. Server 218 may store new anatomical images as they are captured, and/or may store the training dataset. Server 214 may store and/or generate priority list 222B. In another implementation, server 218 is in communication with image server 214 and computing device 204. Server 218 may coordinate between image server 214 and computing device 204, for example, transmitting newly received anatomical images from server 218 to computing device 204 for filtering by visual filter neural network 206C and for insertion into classification neural network 222A for classification thereof (e.g., computation of likelihood of having a visual finding), and transmitting an indication of the computed likelihood from computing device 204 to server 218. Server 218 may compute priority scores and/or rank the anatomical images according to the computed likelihood for computing the priority list. Server 218 may send a list of priority ranked anatomical images and/or the priority list to image server 214, optionally for presentation to a healthcare provider on the display of the client terminal. Client terminal 208 may access the anatomical images of the priority list via server 218, which obtains the images from image server 214. Alternatively, one or more of the described functions of server 218 are performed by computing device 204 and/or imager server 214.

Anatomical image repository 214 that stores anatomical images and/or imaging device 212 that outputs the anatomical images.

Computing device 204 includes or is in communication with a user interface 226 that includes a mechanism designed for a user to enter data (e.g., patient data) and/or view the indications of identified visual findings. Exemplary user interfaces 226 include, for example, one or more of, a touchscreen, a display, a keyboard, a mouse, and voice activated software using speakers and microphone.

Referring now back to FIG. 1, at 102, the visual filter neural network(s) is trained and/or provided. An exemplary process of training the visual filter neural network(s) is described with reference to FIG. 3.

The visual filter neural network is designed to exclude anatomical images that do not depict a target body region (e.g., chest, abdomen, limb) at a target sensor orientation (e.g., AP/PA, lateral, supine, left lateral decubitus), and optionally of a target imaging modality type (e.g., x-ray, 2D CT slices, ultrasound images).

Optionally, multiple visual filter neural network(s) are provided and/or trained. Each visual filter neural network is provided and/or trained to filter images according to a corresponding target classification neural network. For example, one visual filter is designed to filter images being fed into a classification neural network that requires AP/PA chest x-rays, another visual filter is designed to filter images being fed into a classification neural network that requires supine abdominal x-rays, and yet another visual filter is designed to filter images being fed into a classification neural network that requires lateral chest x-rays.

Optionally, the visual filter neural network is installed client-side, optionally on the client terminal that hosts the classification neural network. The client terminal is in communication with the medical imaging storage server over a network. The client-side installation is in contrast to server-side installation, for example, integrated with the PACS server. The client-side installation is independent of the PACS server, and independent of the DICOM® (or other protocol) defining storage of the anatomical images and/or providing metadata for the anatomical images (which may be erroneous). The client-side installation allows installation of multiple visual filter neural networks, each at respective client terminals that host different classification neural networks. Alternatively or additionally, the visual filter neural network is installed server-side, for example, when the classification neural network(s) are executed by the back-end server.

At 104, one or more anatomical images are received, for example, from a medical imaging storage server (e.g., a PACS server), an EMR server, from the anatomical imaging device, and/or from a storage device (e.g., portable storage medium, storage server).

The anatomical images are stored by the medical imaging server according to a medical imaging storage format. For example, the medical imaging server is a PACS server, and the medical imaging storage format is DICOM®. The metadata of DICOM® stores an indication of the target body region and the target sensor orientation. However, such metadata is commonly erroneous. The visual filter neural network described herein rejects anatomical images that do not depict the target body region at the target sensor orientation, independently of the DICOM® metadata. The DICOM® metadata is not necessarily accessed and/or used.

The anatomical images may be, for example, 2D images (e.g., x-ray, ultrasound) and/or 2D slices of 3D images (e.g., of CT and/or MRI scans).

The images may be obtained one at a time, for example, as the anatomical images are captured and stored, and/or may be obtained as a batch, for example, all images captured in the last 15 minutes.

The images may be captured from different anatomical imaging modality machines, and/or captured at different sensor orientations.

Exemplary anatomical imaging device includes an x-ray machine that captures a two dimensional anatomical image.

Anatomical images may be stored as single images, a series of multiple independent images, and/or set of slices (e.g., 2D slices of a 3D volume image). Optionally, each one of the anatomical images is fed into the neural network(s), as described herein.

At 106, the anatomical images are fed into the visual filter neural network. Optionally, the same anatomical images are fed into multiple different visual filter neural networks.

The visual filter neural network outputs a classification category indicating that the respective anatomical image depicts the target body region at the target sensor orientation. The classification category may further include an indication of whether the respective anatomical image is at baseline or rotated relative to the baseline. The classification category may further include an indication of whether the respective anatomical image depicts a target anatomical imaging modality (e.g., x-ray, ultrasound, CT slice). Optionally, a single classification category is indicative of the target sensor orientation and the rotation relative to the baseline, and optionally the depicted body region and optionally the target imaging modality. There may be multiple values for the classification category, each denoting a respective combination of target body region and/or target sensor orientation and/or rotation and/or target imaging modality. For example, AP/PA-90 (denoting AP or PA sensor orientation and rotated clockwise by 90 degrees), and AP/PA-chest-90-degrees-x-ray (denoting AP or PA chest x-ray rotated clockwise by 90 degrees).

Alternatively or additionally, the visual filter neural network outputs another classification category indicating that the respective anatomical image fails to depict one or more of: target body region, target sensor orientation, and target imaging modality. It is noted that a rotation is not necessarily outputted in this case, since rotation may be corrected, while non-target body region, non-target sensor angle, and non-target imaging modality cannot be corrected. Optionally, a single value of the classification category is outputted, for example, REJECT. Alternatively, multiple values of the classification category are outputted, indicative of the body region and/or sensor orientation and/or imaging modality depicted in the image. Such classification results may be used to forward the image to the correct classification neural network.

At 108, a sub-set of the anatomical images classified into the classification category indicative of non-target body region and/or non-target sensor orientation and/or non-target imaging modality are rejected. The rejected images denote irrelevant images, i.e., irrelevant with respect to the classification neural network. The remaining sub-set of anatomical images denote relevant anatomical images i.e., relevant with respect to the classification neural network.

Alternatively or additionally, a sub-set of the anatomical images classified into the classification category indicative of target body region and target sensor orientation and optionally target imaging modality are selected, indicative of relevant images. The remaining images may be rejected and/or ignored.

In one example, the visual filter neural network selects chest images depicting AP and/or PA orientation and optionally x-rays, and/or rejects non-chest x-rays and/or lateral orientation and optionally non-x-ray images. For example, when the visual filter neural network is used with the single-label neural network described with reference to co-filed Application 76282.

The visual filter neural network rejects and/or selects the anatomical images independently of metadata defined by the medical imaging storage format (e.g., DICOM®) associated with the respective anatomical image. For example, the DICOM® metadata is ignored.

At 110, images classified by the visual filter neural network as being rotated relative to baseline are re-rotated to return to the baseline. The rotation may be performed by rotation code. The amount of rotation may be based on the classification results of the visual filter neural network that classifies the amount of rotation of the respective image, for example, when the visual filter neural network computes a 90 degree clockwise rotation from baseline, the image may be rotated 90 degrees counter clockwise to return to baseline (or 270 degrees clockwise).

It is noted that act 110 may be implemented prior to act 108.

At 112, outlier pixel intensity values representing injected content are adjusted. The injected content includes additional data that is not part of the anatomical image itself and/or not a part of the patient's body, for example, a reference object placed beside the patient when taking the image for scaling the image and/or marking the side of the patient, characters (e.g., text, symbols) added to the image. The characters may be, for example, the name of the patient, ID of the patient, date of image.

Optionally, image for which the adjustment of pixel intensity value is performed has a pixel depth that is different than a pixel depth of the respective image when presented on a display. For example, the pixel intensity value is stored in for example the range 10-16 bits and presented as 8 bits. The adjustment is performed for the stored image with the higher pixel depth.

Optionally, the outlier pixel intensity values representing injected content are identified based on an analysis of a created histogram of pixel intensity values. The histogram partition may be selected, for example, based on a pre-defined number of bins, and/or by code according to an analysis of the pixel intensity values of the image. For example, when the pixel intensity value is stored as a 16 bit integer, a 75 bin histogram may be used. The outlier pixel intensity values are selected based on one or two extreme bins of the histogram that are spaced apart from another bin by an empty bin that does not include any pixels. When the two extreme bins are adjacent (i.e., not spaced apart by an empty bin), no fix is necessary. When the two extreme bins are spaced apart, a fix is performed. The outlier pixel intensity values of the identified pixels may be adjusted to values computed as a function of non-outlier pixel intensity values. Optionally, the values are computed as a function of the other bin and all pixels in the respective image. The function may be computed, for example, as: (i) a minimum of the pixel intensity values in the other bin, less a constant multiplied by the median pixel intensity values of all pixels in the respective image, and (ii) a maximum of the pixel intensity values in the other bin, added to a constant multiplied by the median pixel intensity values of all pixels in the respective image, and (iii) a smallest interest such that two raised to the smallest integer minus one is greater than the maximum of the pixel intensity values in the other bin. For example, to correct the left most bin in the case that two left most bins that are spaced apart with one or more empty bins, the following exemplary function may be used:

$$\text{Fixed value}=\min(B)-0.005*\text{median(all image)},$$

where the fixed value is a computed intensity value for replacing the current pixel intensity values of the left most bin, and B denotes the bin closest to the most extreme bin, optionally to the left most bin (i.e., the second most extreme bin, the first non-empty bin after the empty next to the most extreme left bin.)

An example of using the above equation to correct an image is now provided. For example, the minimal gray level (i.e., pixel intensity value) in bin B is determined to be 123. The median pixel intensity value of all pixels in the image is determined to be 789. All pixel intensity values falling within the left most bin are adjusted to the fixed value of: $123-0.0005*789=119$.

In another example, to correct the right most bin in the case of the two right most bins being spaced apart with one or more empty bins, the following exemplary function may be used:

$$\text{Fixed value}=\min(2^m-1,\max(C)+0.005*\text{median(all image)})$$

where C denotes the bin closest to the most extreme bin, optionally to the right most bin (i.e., the second most extreme bin, the first non-empty bin after the empty next to the most extreme right bin.)

It is noted that in the equation, the fixed value for the outlier pixels is clipped by $2^m-1$, where m denotes the smallest integer such that $2^m > \max(C)$.

Figure 4:
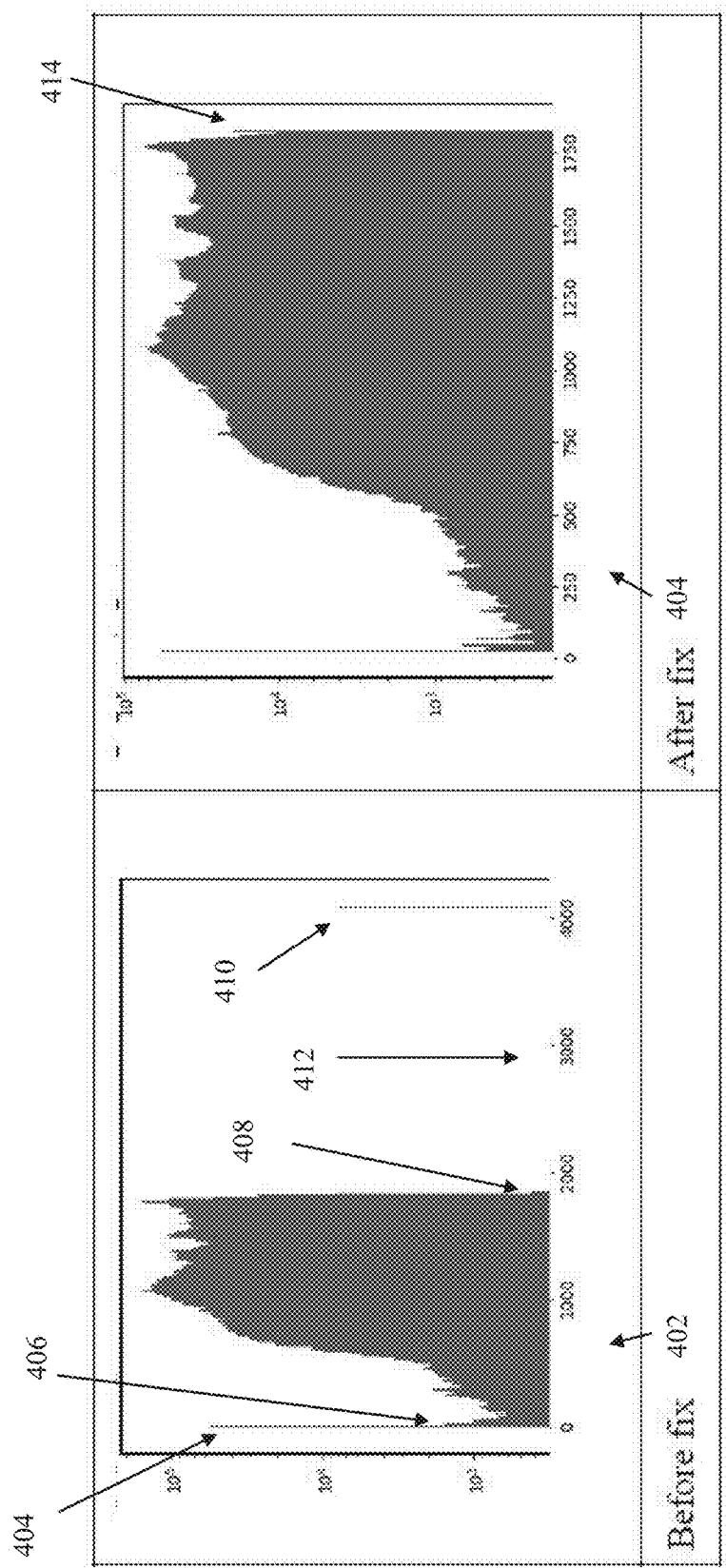
FIG. 4 is a schematic of a histogram computed for the original pixel intensity values, and an adjusted histogram that corrects for injected content, in accordance with some embodiments of the present invention.

Reference is now made to FIG. 4, which is a schematic of a histogram 402 computed for the original pixel intensity values, and an adjusted histogram 404 that corrects for injected content, in accordance with some embodiments of the present invention.

Histogram 402 is computed for the original pixel intensity values, as described herein. It is noted that since the two left most non-empty bins are denoted 404 and 406 are not separated by at least one empty bin, no fix is performed for bins 404 and 406. Since right most bins 408 410 are separated by at least one empty bin 412 (in fact as shown, many empty bins 412), a fix is performed for bin 410 by adjusting the pixel intensity values of pixels falling in bin 410 according to the equation $$\text{Fixed value}=\min(2^m-1,\max(C)+0.005*\text{median(all image)}),$$

resulting in changing bin 410 of histogram 402 into bin 414 of histogram 404. It is noted that the empty bins are irrelevant and are excluded from the x-axis of histogram 404.

Referring now back to FIG. 1, at 112, it is noted that act 112 may be implemented before acts 106, and/or 110. Implement act 112 after 106 and 110 reduces processing resource requirements, since anatomical images that are excluded by the filter not are processed for adaptation of their outlier pixel intensity values.

Once the set of images have been filtered and optionally processed by adjusting the values of the pixel intensity values denoting injected content, the set of images may be used to create a training dataset for training a classification neural network (acts 114-116) and/or fed into the trained classification neural network (act 118-124). It is noted that the classification neural network trained using the training dataset that includes the filtered images may be fed filtered anatomical images. The same classification neural network trained in act 116 may be fed filtered images in act 118.

At 114, a training dataset of filtered anatomical medical images (i.e., not rejected and/or selected by the visual filter neural network) and optionally images rotated to the baseline, is created. Each image the training dataset is labeled with a label indicative of the desired classification performed by the classification neural network.

At 116, the classification neural network is trained according to the created training dataset.

At 118, the post-filtering anatomical images (i.e., the remaining non-rejected and/or selected sub-set of the anatomical images) are fed into the classification neural network.

Optionally, where multiple visual filter neural networks and corresponding multiple classification neural networks are implemented, images passed through respective visual filter neural networks are fed into the corresponding classification neural network.

Optionally, the classification neural network is obtained according to act 116, i.e., trained using a training dataset created from anatomical images filtered using the visual filter neural network (act 114), optionally the same visual filter neural network as in act 106.

The classification neural network may output an indication of likelihood of a visual finding type being depicted in the respective anatomical image. The visual finding type may be indicative of an acute medical condition, which may require early and rapid treatment to prevent or reduce complications and/or morbidity arising from delayed treatment. For example, detecting an indication of pneumothorax is AP and/or PA chest x-rays.

Optionally, the classification neural network is implemented as a single-label neural network computed by fine-tuning and/or retraining a trained multi-label neural network. The multi-label neural network is trained according to a single-label training dataset of anatomical images labeled with an indication of the visual finding. The multi-label neural network is trained to compute likelihood of each of multiple visual findings being depicted in the fed image, based on a multi-label training dataset storing anatomical images labeled with an indication of respective depicted visual finding types. The images included in the single-label training dataset and/or the multi-label training dataset are optionally images filtered by the visual filter neural network. Additional details of the single-label neural network and the multiple-label neural network are described with reference to co-filed Application.

At 120, when multiple anatomical images are fed into the single-label neural network, instructions for creating a triage list may be generated, and/or the triage list may be generated.

The triage list includes anatomical images determined as likely to depict the visual finding type(s) likely to be depicted as outputted by the classification neural network(s). The triage list may be for directing a priority of manual review by a human reviewer (e.g., radiologist).

Optionally, the triage list is ranked by decreasing likelihood of the indication of the visual finding type(s) based on a confidence score computed by the classification neural network(s). For example, images having a higher computed probability score of depicting the visual finding type(s) are ranked higher in the list than other images having lower probability scores. When multiple classification neural networks analyze the same image (which is fed through different corresponding visual filter neural networks) to detect different visual finding types, an aggregated priority score may be computed. The aggregated score may be weighed, for example, according to clinical urgency of the medical condition associated with the respective visual finding. The ranking of images may be according to the aggregated priority score.

As used herein, the term priority list and triage list are interchangeable.

The triage list is for manual review by a human user (e.g., radiologist, emergency room physician, surgeon) of respective target anatomical images computed as likely depicting the indication of the visual finding type.

The priority list may be created by the computing device, and provided to image server, and/or the client terminal. In another implementation, the computing device provides instructions for creating the priority list to the image server, and the image server crates the priority list.

The list may be viewed by the user (e.g., within the PACS viewer) optionally for manual selection of images for viewing, and/or may define automatic sequential loading of images for viewing by the user (e.g., within the PACS viewer).

At 122, the user may manually view images in the priority list, optionally according to the ranking.

At 124, the acute medical condition may be diagnosed and/or treated. The visual finding type is a sign of the acute medical condition. The patient may be treated for the acute medical condition.

For example, when the visual finding type of pneumothorax is found in the chest x-ray by the classification neural network, and the finding is confirmed by manual visual inspection by a radiologist, the patient may be diagnosed and/or treated, for example, by insertion of a needle or chest tube to remove the excess air.

Reference is now made to FIG. 3. At 302, a target body region (e.g., chest, abdomen, limb, head) and a target sensor orientation (e.g., AP, PA, lateral, left lateral decubitus) for target anatomical image(s) are received.

The target body region and the target sensor orientation are defined by the target classification neural network into which the target anatomical images are fed.

When multiple classification neural networks are implemented, multiple combinations of the target body region and target sensor orientation are received.

Optionally, in addition to the target body region and a target sensor orientation, a target anatomical imaging modality is defined according to the target classification neural network.

At 304, anatomical images are obtained.

The anatomical images may be obtained, for example, from a data storage server, a publicly available image dataset, and/or other sources.

Optionally, images may be preprocessed to increase the number of training images and/or variety of the training image, for example, with the following additional augmentations: random horizontal flip, random crop, random rotation, and random zoom.

At 306, a training dataset for training the visual filter neural network is created.

Optionally, each one of the anatomical images is associated with a respective label indicative of a target body region and a target sensor orientation. When multiple target body regions and/or target sensor orientations are desired (e.g., for different classification neural networks) and/or when the actual value of the target body region and/or actual value of the target sensor orientation is not known, each anatomical image may be labeled with an indication of the actual depicted body region and depicted sensor orientation. When the target body region and target sensor orientation is defined (e.g., according to the classification neural network), the label may be indicative of whether the body region and sensor orientation are according to the defined target, or non-target.

Optionally, each of the anatomical images is labeled with an indication of a rotation relative to a baseline.

Optionally, each of the anatomical images is further labeled with an indication of anatomical imaging modality type, for example, the value of the actual anatomical modality type, and/or an indication of whether the anatomical imaging modality type is target or non-target.

The labeling may be performed, for example, manually by a user, and/or automatically based on DICOM® metadata with a review by the user to check for errors in the DICOM® metadata.

At 308, the visual filter neural network is trained based on the training dataset. Multiple visual filter neural networks may be trained on the same training dataset, according to their respective requirements for body region and/or sensor orientation and/or imaging modality type.

The visual filter neural network is trained for classifying a target anatomical image into a classification category indicative of the target body region depicted at the target sensor angle and optionally at the target imaging modality type, and optionally the rotation relative to the baseline, or into another classification category indicative of non-target body region and/or non-target sensor orientation and/or non-target anatomical imaging modality.

The target anatomical image is rejected when classified into the classification category indicative of non-target body region and/or a non-target sensor orientation and/or non-target anatomical imaging modality type.

Optionally, additional code is provided in association with the visual filter neural network for rotating target anatomical images determined to be rotated back to the baseline.

The anatomical images that are not rejected and/or selected by the visual filter neural network are inputted into the classification neural network for determining likelihood of the visual finding type being depicted therein, as described herein.

At 310, the trained visual filter neural network(s) are provided, for example, locally stored and/or transmitted to the computing device.

Figure 5:
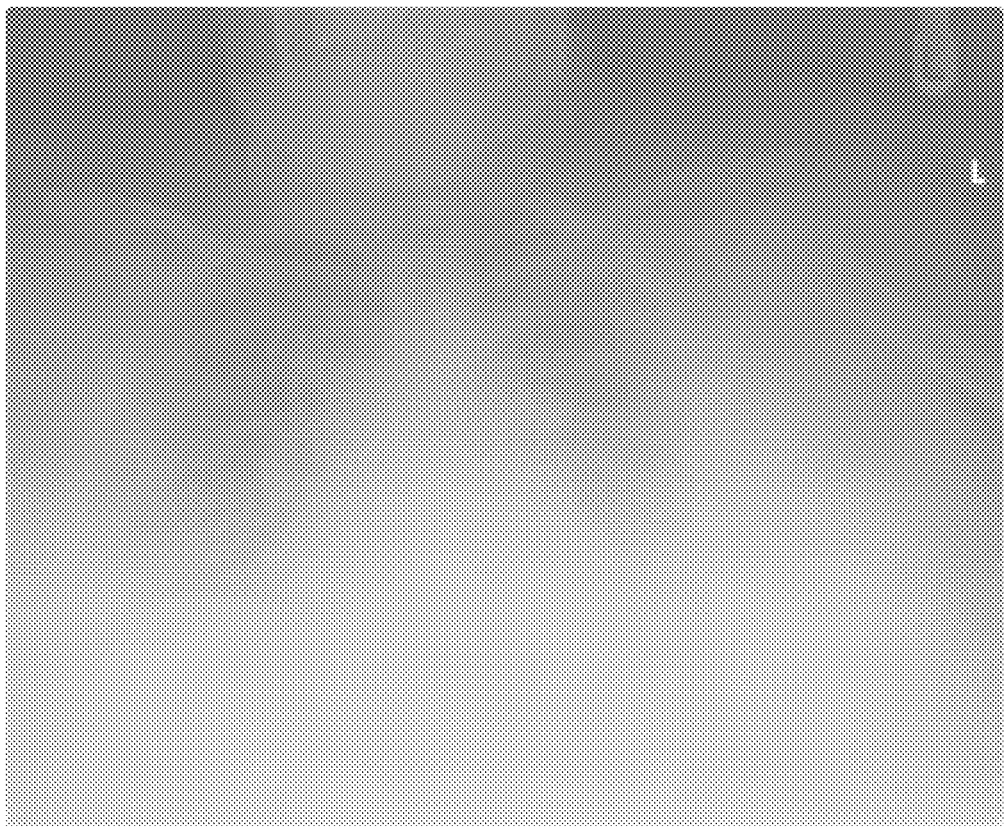
FIG. 5 includes an AP/PA chest x-ray before adjustment of pixel intensity values denoting injected content, and an x-ray depicting the AP/PA chest x-ray after adjustment of pixel intensity values denoting injected content, in accordance with some embodiments of the present invention.
Figure 5:
Figure 5:
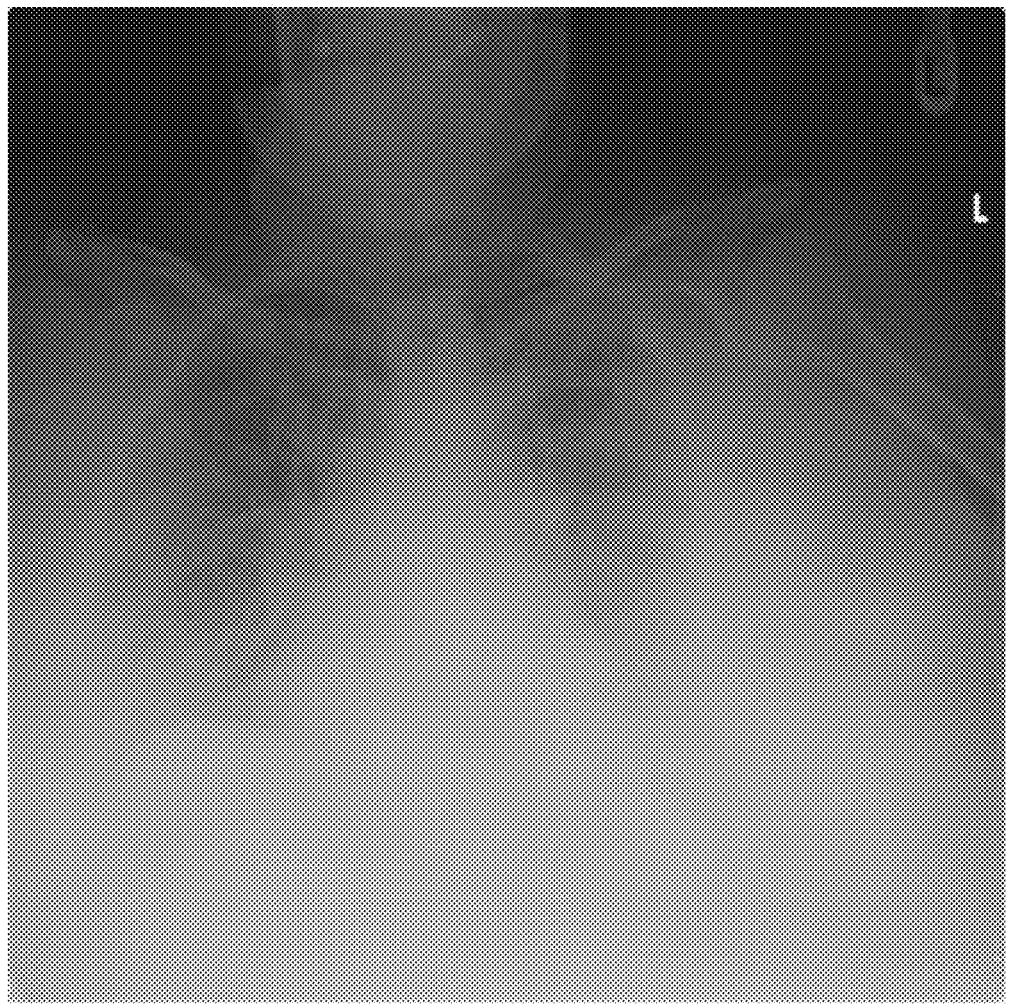

Reference is now made to FIG. 5, which includes an AP/PA chest x-ray before adjustment of pixel intensity values denoting injected content 502, and an x-ray 504 depicting the AP/PA chest x-ray after adjustment of pixel intensity values denoting injected content, as described herein, in accordance with some embodiments of the present invention. As seen, x-ray 504 depicts an improvement in dynamic range. The accuracy of detection of minor and/or fine visual features, such as pneumothorax, by the classification neural network is improved when the classification neural network is fed x-ray 504 in comparison to the classification neural network being fed x-ray 502.

EXAMPLES

Reference is now made to the following examples, which together with the above descriptions illustrate some implementations of the systems, methods, apparatus, and/or code instructions described herein in a non limiting fashion.

Inventors performed a computational evaluation according to the systems and/or methods and/or apparatus and/or code instructions described herein, based on the features and/or system components discussed with reference to FIGS. 1-3.

Reference is now made to the following examples of creating a visual filter neural network, which together with the above descriptions illustrate some implementations of the systems, methods, apparatus, and/or code instructions described herein in a non limiting fashion.

Figure 6:
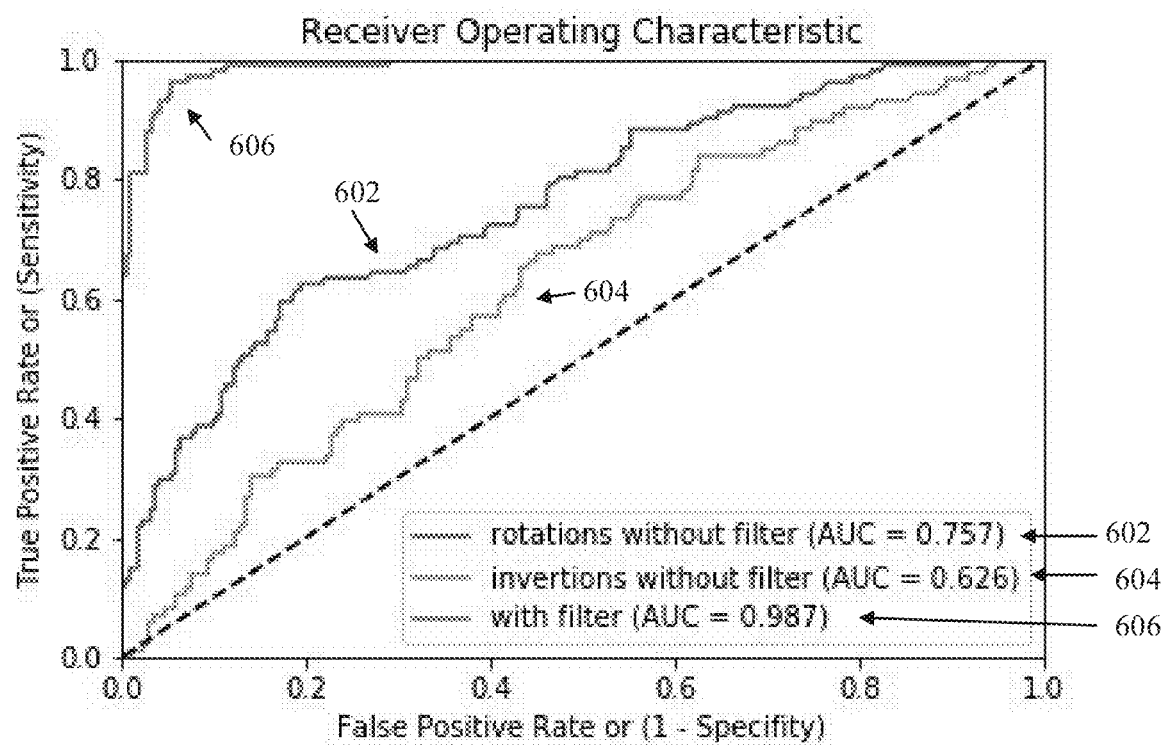
FIG. 6 is a graph of ROC curves computed for the experiments for computationally evaluating the visual filter neural network in increasing classification accuracy of a classification neural network, in accordance with some embodiments of the present invention.

Inventors performed computational evaluations for providing quantitative evidence that the neural network filter described herein improves accuracy of classification by the classification neural network. In particular, the evaluation focused on using a neural network that detects an indication of pneumothorax in chest x-rays. Three experiments were performed. Reference is also made to FIG. 6, which is a graph of ROC curves computed for the experiments for computationally evaluating the visual filter neural network in increasing classification accuracy of a classification neural network, in accordance with some embodiments of the present invention.

Experiment 0 (Baseline):
Data:
  Curated internal validation set (internal validation 2801, 323 chest serieses including clalit, rapid rad and intermountain data sources).
  All images in the baseline dataset were randomly rotated at 90, 180, 270 degrees.
Neural networks:
  pnx_net (i.e., classification neural network) with xray_filter (i.e. visual filter neural network). All rotations were fixed.
Results:
  AUC=0.987 (line 606 in the graph of FIG. 6)
  Specificity and sensitivity at the production operating point are 0.945 and 0.940 correspondingly.

Experiment 1 (random rotations):
Data:
  As in experiment 0
Neural network:
  pnx_net (i.e., classification neural network), without fixing rotations. The visual filter neural network was not used.
Results:
  AUC=0.757 (line 602 in the graph of FIG. 6)
  specificity and sensitivity at the production operating point are 0.982 and 0.188 correspondingly.

Experiment 2 (grayscale invertions):
Data:
  Curated internal validation set (internal validation 2801, 323 chest serieses including clalit, rapid rad and intermountain data sources).
  All images in the baseline dataset were inverted (e.g. were intentionally assigned monochrome 1 photometric interpretation not supported by the pnx classification neural network)
Neural network:
  pnx_net (i.e., classification neural network) without correction of photometric interpretation, and without using the visual filter neural network.
Results:
  AUC=0.626 (line 604 in FIG. 6)
  Specificity and sensitivity at the production operating point are 0.965 and 0.058 correspondingly.

Experiment 3 (not-chest):
Data:
    271 series containing not-chest body parts (clalit, rapid rad)
Neural network:
    pnx_net (i.e., classification neural network) without filtering out not chest images
Results:
    Specificity at the production operating point is: 0.897.
        Running pnx_net with xray filter on the same not-chest data would result in 0 false positives since all of the images would have been correctly filtered out.
    Conclusions: The above 3 experiments demonstrate that the visual filter neural network significantly improves the accuracy of the classification neural network (in this case in detecting pneumothorax) in the presence of rotated, inverted, and not chest images.

Inventors performed additional computational evaluations of the visual filter created according to the systems and/or methods and/or apparatus and/or code instructions described herein, based on the features and/or system components discussed with reference to FIGS. 1-3.

The visual filter neural network was designed to receive an anatomical image (i.e., 2D image) as input, and to output one of the following classification categories (also referred to herein as labels): NOT_CHEST, PA-0, PA-1, PA-2, PA-3, AP-0, AP-1, AP-2, AP-3, LATERAL_LEFT-0, LATERAL_LEFT-1, LATERAL_LEFT-2, LATERAL_LEFT-3, LATERAL_RIGHT-0, LATERAL_RIGHT-1, LATERAL_RIGHT-2, and LATERAL_RIGHT-3.

The prefixes PA, AP, LATERAL_LEFT, LATERAL_RIGHT indicate the sensor orientation. The non-zero numbers (1, 2, 3) denote an amount of rotation of the image, clockwise, in multiples of 90 degrees. i.e. PA-3 means the image is a PA view of a chest x-ray that was rotated by 270 degrees.

The input image into the visual filter neural network has size 192×192.

The model architecture used as a basis for the visual filter neural network was Inception V3.

The training set had 20,000 images.

AP, PA, LATERAL, and NON-CHEST image labels were obtained by processing the DICOM® tag. The LATERAL images were assigned LATERAL_RIGHT and LATERAL_LEFT labels by manual inspection. Rotated images (with associated rotation labels) were generated artificially and on-the-fly during training.

The model was validated against a held-out validation set and achieved an accuracy of over 99%.

Reference is now made to the following examples of adjusting outlier pixel intensity values of images prior to processing by the classification neural network, which together with the above descriptions illustrate some implementations of the systems, methods, apparatus, and/or code instructions described herein in a non limiting fashion.

Inventors performed a computational evaluation of the images for which pixel intensity values were adjusted according to the systems and/or methods and/or apparatus and/or code instructions described herein, based on the features and/or system components discussed with reference to FIGS. 1-3.

A set of 177,000 anatomical images was created, wherein the DICOM® bit depth is different than the actual bit depth, for example 10 vs. 12. A subset of 50 images was selected as a compact validation dataset, termed OPIF. The process for adjusting outlier pixel intensity values was run on the OPIF validation dataset. The following plots were generated for every image: original image converted to 8-bit (using min-max), histogram of original full bit depth image, fixed image converted to 8-bit (using min-max), and histogram of fixed full bit depth image. The results were manually analyzed. First, it verified that the histogram was fixed correctly and that the image does not contain outlier pixel intensity values. In addition, the conversion of the fixed image to 8-bit was verified.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical images will be developed and the scope of the term anatomical image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for prioritizing patients for treatment for an acute medical condition requiring early and rapid treatment thereof based on a created a triage list of inference anatomical images likely depicting a visual finding type indicative of the acute medical condition, comprising:
    at least one hardware processor executing a code for:
    feeding each one of a plurality of inference anatomical images into a visual filter neural network for inference of each one of the plurality of inference anatomical images by outputting a classification category indicative of a target body region depicted at a target sensor orientation and a rotation relative to a baseline;
    rejecting a sub-set of the plurality of inference anatomical images classified into another classification category;
    rotating to the baseline a remaining sub-set of the plurality of inference anatomical images classified as rotated relative to the baseline by the visual filter neural network;
    identifying pixels for each respective image of the plurality of inference anatomical images having outlier pixel intensity values denoting an injection of content injected into the plurality of inference anatomical images after capture of the plurality of inference anatomical images;
    adjusting the outlier pixel intensity values of the identified pixels denoting the injection of content injected into the plurality of inference anatomical images after capture of the plurality of inference anatomical images to values computed as a function of non-outlier pixel intensity values;
    feeding each one of the remaining sub-set of the plurality of inference anatomical images with adjusted outlier pixel intensity values of the identified pixels denoting the injection of content injected into the plurality of inference anatomical images after capture of the plurality of inference anatomical images into a classification neural network for inference of the plurality of inference anatomical images by detecting the visual finding type; and
    generating instructions for creating a triage list for which the classification neural network detected the indication for a plurality of patients,
    wherein the plurality of patients likely suffering from the acute medical condition denoted by the indication are selected for early and rapid treatment thereof based on the triage list created based on the feeding the plurality of inference anatomical images into the visual filter neural network, the rejecting, the rotating, the identifying pixels, the adjusting, and the feeding inference anatomical images into the classification neural network.

2. The system of claim 1, wherein accuracy of the classification neural network in detecting the visual finding type indicative of the acute medical condition is increased for the remaining sub-set of the plurality of inference anatomical images in comparison to detecting the visual finding type for the plurality of inference anatomical images by the classification neural network without rejection of any inference anatomical images by the visual filter neural network.

3. The system of claim 1, wherein accuracy of the classification neural network in detecting the visual finding type indicative of the acute medical condition is increased for the remaining sub-set of the plurality of inference anatomical images with adjusted outlier pixel intensity values and rotation to baseline, in comparison to detecting the visual finding type for the plurality of inference anatomical images by the classification neural network without rejection of any inference anatomical images by the visual filter neural network, without adjustment of outlier pixel intensity values, and without rotation to baseline.

4. The system of claim 1, further comprising at least one of:
    diagnosing the acute medical condition and treating the patient for the acute medical condition.

5. The system of claim 1, wherein the visual filter neural network selects chest x-rays depicting at least one of AP and PA orientation, and rejects at least one of non-chest x-rays and lateral orientation.

6. The system of claim 1, wherein the visual filter neural network is installed client-side, on a client terminal in communication with the medical imaging storage server over a network, wherein the client terminal hosts the classification neural network.

7. The system of claim 1, wherein a single classification category is indicative of the depicted body region, the target sensor orientation and the rotation relative to the baseline.

8. The system of claim 1, wherein the classification neural network is trained according to a training dataset of training anatomical medical images that were not rejected by the visual filter neural network, had outlier pixel intensity values denoting injected content adjusted, and rotated to the baseline.

9. The system of claim 1, wherein the visual filter neural network outputs the classification category further indicative of a target imaging modality type or the another classification category further indicative of a non-target imaging modality type, wherein the rejected sub-set of the plurality of inference anatomical images include anatomical images classified into the another classification category.

10. The system of claim 1, wherein the plurality of inference anatomical images are stored by a medical imaging server according to a medical imaging storage format, and wherein the visual filter neural network rejects the sub-set of the plurality of inference anatomical images independently of metadata defined by the medical imaging storage format and associated with the respective inference anatomical image.

11. The system of claim 10, wherein the medical imaging server comprise a PACS server, the medical imaging storage format is DICOM®, and the metadata of DICOM® stores an indication of the target body region and the target sensor orientation.

12. The system of claim 1, wherein the adjusting is performed for the respective image having outlier pixel intensity values stored with a pixel depth, that is different than a pixel depth of the respective image when presented on a display.

13. The system of claim 1, further comprising:
computing, for each respective image, a histogram of pixel intensity values,
wherein the outlier pixel intensity values are selected based on one or two extreme bins of the histogram that are spaced apart from another bin by an empty bin that does not include any pixels.

14. The system of claim 13, wherein the outlier pixel intensity values are adjusted to a value computed as a function of the another bin and all pixels in the respective image.

15. The system of claim 14, wherein the function is computed one of: (i) a minimum of the pixel intensity values in the another bin, less a constant multiplied by the median pixel intensity values of all pixels in the respective image, and (ii) a maximum of the pixel intensity values in the another bin, added to a constant multiplied by the median pixel intensity values of all pixels in the respective image, and (iii) a smallest interest such that two raised to the smallest integer minus one is greater than the maximum of the pixel intensity values in the another bin.

16. The system of claim 1, wherein the classification neural network comprises a single-label neural network computed by at least one of fine-tuning and retraining a trained multi-label neural network according to a single-label training dataset of a plurality of anatomical images labeled with an indication of the visual finding type, wherein the multi-label neural network is trained to compute likelihood of each of a plurality of visual finding types based on a multi-label training dataset storing a plurality of anatomical images labeled with the plurality of visual finding types.

17. The system of claim 1, further comprising:
providing a plurality of classification neural networks, each designed for processing anatomical images of a certain combination of a plurality of combinations of target body region and target sensor orientation;
providing a plurality of visual filter neural networks, each designed for classification of anatomical images into a classification category indicative of the certain combination of the plurality of combinations,
wherein each certain visual filter neural network corresponds to a certain classification neural network; and
feeding the plurality of inference anatomical images into each one of the plurality of classification neural networks to obtain a respective sub-set of the plurality of inference anatomical images, and feeding each respective sub-set of the plurality of inference anatomical images into the corresponding classification neural network.

18. A system for training a visual filter neural network for selection of inference anatomical images for inputting into a classification neural network for detecting a visual finding type indicative of an acute medical condition for early and rapid treatment thereof, comprising:
receiving a target body region and a target sensor orientation of a target anatomical image defined by the classification neural network;
creating a training dataset by labeling each one of a plurality of anatomical images stored by a medical imaging storage server with a respective label indicative of a target body region captured at a target sensor orientation defined by the classification neural network and a rotation relative to a baseline, or with a respective label indicative of at least one of a non-target body region and a non-target sensor orientation; and
training the visual filter neural network based on the training dataset, for inference of a target inference anatomical image inputted into the visual filter neural network, into a classification category indicative of the target body region depicted at the target sensor angle and the rotation relative to the baseline, or into another classification category indicative of at least one of a non-target body region and a non-target sensor orientation,
wherein the target inference anatomical image is rejected when classified into the another classification category, and the target inference anatomical image is rotated to the baseline according to the classification as rotated relative to the baseline obtained from the visual filter neural network and inputted into the classification neural network for inference of the target anatomical image by detecting the visual finding type when classified into the target body region depicted at the target sensor angle and the rotation relative to the baseline by the visual filter neural network.

19. A system for increasing accuracy of a classification neural network in detecting a visual finding type indicative of an acute medical condition for early and rapid treatment thereof, comprising:
at least one hardware processor executing a code for:
receiving a plurality of inference anatomical images from a medical imaging storage server;
feeding each one of the plurality of inference anatomical images into a visual filter neural network for inference of each one of the plurality of inference anatomical images by outputting a classification category indicative of a target body region depicted at a target sensor orientation and a rotation relative to a baseline defined by the classification neural network, or another classification category indicative of at least one of a non-target body region and a non-target sensor orientation;
rejecting a sub-set of the plurality of inference anatomical images classified into the another classification category, to obtain a remaining sub-set of the plurality of anatomical images;
rotating to the baseline the remaining sub-set of the plurality of inference anatomical images classified as rotated relative to the baseline by the visual filter neural network;

creating a training dataset from the remaining sub-set of the plurality of inference anatomical images; and training a classification neural network according to the training dataset for inference of a target inference anatomical image by detecting the visual finding type indicative of the acute medical condition for early and rapid treatment thereof.

20. A system for increasing accuracy of a classification neural network in detecting a visual finding type indicative of an acute medical condition for early and rapid treatment thereof, comprising:

at least one hardware processor executing a code for:

receiving a plurality of inference anatomical images from a medical imaging storage server;

feeding each one of the plurality of inference anatomical images into a visual filter neural network for inference of each one of the plurality of inference anatomical images by outputting a classification category indicative of a target body region depicted at a target sensor orientation and a rotation relative to a baseline defined by the classification neural network, or another classification category indicative of at least one of a non-target body region and a non-target sensor orientation;

rejecting a sub-set of the plurality of inference anatomical images classified into the another classification category, to obtain a remaining sub-set of the plurality of inference anatomical images;

rotating to the baseline the remaining sub-set of the plurality of inference anatomical images classified as rotated relative to the baseline by the visual filter neural network; and feeding each one of the remaining sub-set of the plurality of inference anatomical images into the classification neural network for inference of the plurality of inference anatomical images by detecting the visual finding type indicative of the acute medical condition for early and rapid treatment thereof.

* * * * *